US012327334B2

(12) United States Patent
Broadwater et al.

(10) Patent No.: US 12,327,334 B2
(45) Date of Patent: Jun. 10, 2025

(54) CAPTURING MULTI-SPECTRAL IMAGES

(71) Applicant: THE JOHNS HOPKINS UNIVERSITY, Baltimore, MD (US)

(72) Inventors: Joshua Broadwater, Laurel, MD (US); Amit Banerjee, Silver Spring, MD (US); Simon C. Mathews, Baltimore, MD (US); Pankaj Jay Pasricha, Ellicott City, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 18/861,344

(22) PCT Filed: Jul. 6, 2023

(86) PCT No.: PCT/US2023/026969
§ 371 (c)(1),
(2) Date: Oct. 29, 2024

(87) PCT Pub. No.: WO2024/025712
PCT Pub. Date: Feb. 1, 2024

(65) Prior Publication Data
US 2025/0117889 A1    Apr. 10, 2025

Related U.S. Application Data

(60) Provisional application No. 63/392,631, filed on Jul. 27, 2022.

(51) Int. Cl.
*G06V 10/143* (2022.01)
*G01N 33/574* (2006.01)
*G06T 5/50* (2006.01)

(52) U.S. Cl.
CPC ............ *G06T 5/50* (2013.01); *G01N 33/574* (2013.01); *G06V 10/143* (2022.01); *G06T 2207/20221* (2013.01)

(58) Field of Classification Search
CPC ............ G06T 5/50; G06T 2207/20221; G01N 33/574; G06V 10/143
See application file for complete search history.

(56) References Cited

U.S. PATENT DOCUMENTS

| | | | |
|---|---|---|---|
| 8,802,442 B2* | 8/2014 | Wheeldon | G01N 21/75 436/66 |
| 10,575,830 B2* | 3/2020 | Attar | G06T 7/0014 |

(Continued)

OTHER PUBLICATIONS

Matos, T. (Authorized officer), International Search Report and Written Opinion in corresponding International Application No. PCT/US2023/026969 mailed on Oct. 2, 2023, 7 pages.

(Continued)

*Primary Examiner* — Phuoc Tran
(74) *Attorney, Agent, or Firm* — MH2 Technology Law Group LLP

(57) ABSTRACT

A method for performing a screening includes illuminating a sample with light from a screen of a system at a first wavelength while the system is at a predetermined position with respect to the sample. The method also includes capturing a first image of the sample using a camera of the system while the system is at the predetermined position and the sample is illuminated with the light at the first wavelength. The method also includes illuminating the sample with the light from the screen at a second wavelength while the system is at the predetermined position. The method also includes capturing a second image of the sample using the camera while the system is at the predetermined position and the sample is illuminated with the light at the second wavelength. The method also includes combining the first and second images to produce a multispectral image.

20 Claims, 7 Drawing Sheets

(56) References Cited

U.S. PATENT DOCUMENTS

| | | |
|---|---|---|
| 11,640,101 B2 * | 5/2023 | Weaver ................ G06V 30/194 362/555 |
| 2015/0185151 A1 | 7/2015 | Utzinger et al. |
| 2020/0264098 A1 | 8/2020 | Huang |
| 2020/0281454 A1 | 9/2020 | Refai et al. |
| 2021/0011001 A1 | 1/2021 | Chou et al. |
| 2021/0334969 A1 | 10/2021 | Al-maadeed et al. |

OTHER PUBLICATIONS

Baharlou, S. (Authorized officer), International Preliminary Report on Patentability in corresponding International Application No. PCT/US2023/026969 mailed on Feb. 6, 2025, 6 pages.

* cited by examiner

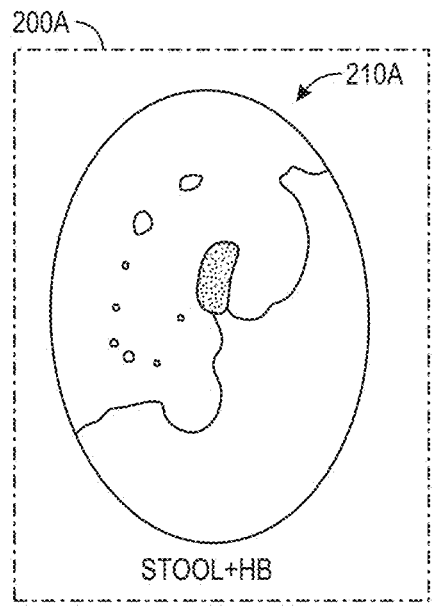 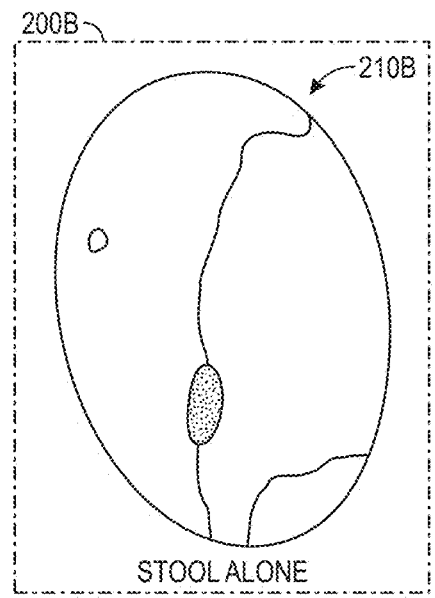
FIG. 2A  FIG. 2B
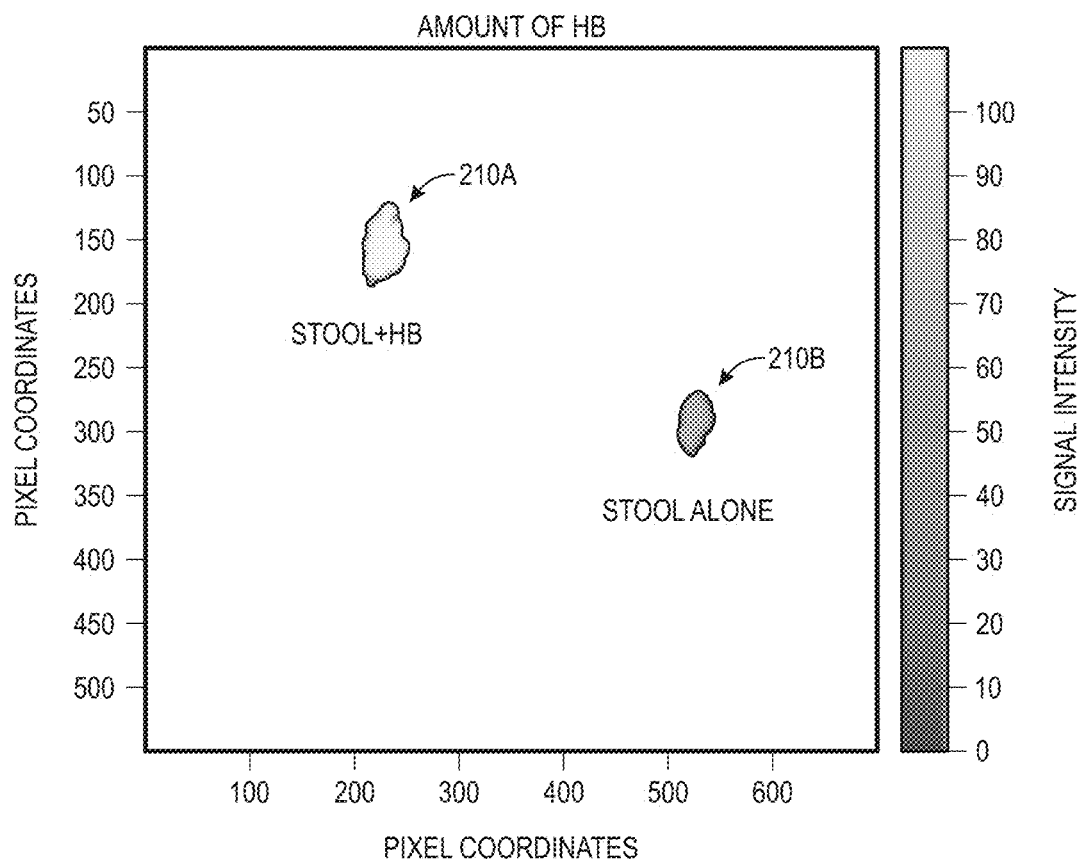
FIG. 3

CAPTURING MULTI-SPECTRAL IMAGES

CROSS-REFERENCE TO RELATED APPLICATIONS

This application is the national stage entry of International Patent Application No. PCT/US2023/026969, filed on Jul. 6, 2023, and published as WO 2024/025712 A1 on Feb. 1, 2024, which claims the benefit of U.S. Provisional Patent Application No. 63/392,631, filed on Jul. 27, 2022, which are hereby incorporated by reference in their entireties.

FIELD OF THE DISCLOSURE

The present disclosure relates generally to systems and methods for capturing multi-spectral images. More particularly, the present disclosure relates to systems and methods for capturing and analyzing multi-spectral images using a phone to detect a biomarker in a sample as part of a colorectal cancer (CRC) screening.

BACKGROUND OF THE DISCLOSURE

A colonoscopy is an endoscopic procedure that is commonly used to screen for colorectal cancer or to detect other abnormalities in the large intestine and rectum. During a colonoscopy, a long, flexible tube (i.e., a colonoscope) is inserted into the rectum. A tiny video camera at the tip of the tube allows the doctor to view the inside of the entire colon. If necessary, polyps or other types of abnormal tissue can be removed through the scope during a colonoscopy. Tissue samples (e.g., biopsies) can be taken during a colonoscopy as well. However, it would be useful to have systems and methods that provide an alternative to screening for colorectal cancer that is both convenient and non-invasive.

SUMMARY

A method for performing a screening is disclosed. The method includes illuminating a sample with light from a screen of a system at a first wavelength while the system is at a predetermined position with respect to the sample. The method also includes capturing a first image of the sample using a camera of the system while the system is at the predetermined position and the sample is illuminated with the light at the first wavelength. The method also includes illuminating the sample with the light from the screen at a second wavelength while the system is at the predetermined position. The method also includes capturing a second image of the sample using the camera while the system is at the predetermined position and the sample is illuminated with the light at the second wavelength. The method also includes combining the first and second images to produce a multi-spectral image. The method also includes measuring a spectral feature in the multispectral image.

A method for performing a colorectal cancer (CRC) screening is also disclosed. The method includes determining a position of a system relative to a sample. The system includes a phone or a tablet with a front side having a screen and a camera located above the screen. The sample includes stool, saliva, sweat, blood, urine, skin, or a combination thereof. The method also includes instructing a user holding the phone or tablet to move the phone or tablet into a predetermined position in response to the determined position. Moving the phone or tablet varies a distance between the front side and the sample, varies an angle between the front side and the sample, or both. The method also includes illuminating the sample with the light from the screen at a first wavelength while the phone or tablet is at the predetermined position. The method also includes capturing a first image of the sample using the camera while the phone or tablet is at the predetermined position and the sample is illuminated with the light at the first wavelength. The method also includes illuminating the sample with the light from the screen at a second wavelength while the phone or tablet is at the predetermined position. The sample is illuminated with the light at the second wavelength after the first image has been captured. The first and second wavelengths are different. The method also includes capturing a second image of the sample using the camera while the phone or tablet is at the predetermined position and the sample is illuminated with the light at the second wavelength. The method also includes combining the first and second images to produce a multispectral image. The method also includes measuring a spectral feature at each pixel in the multispectral image using a spectral processing algorithm running on the system. The method also includes determining a concentration of a biomarker in the sample based at least partially upon the spectral feature. The biomarker includes hemoglobin, bilirubin, calprotectin, albumin, fatty acid, hydrogen sulfide, or a combination thereof. The method also includes determining that a person from whom the sample was taken is at increased risk for a condition based at least partially upon the concentration of the biomarker.

A system for performing a screening is also disclosed. The system includes a screen configured to emit light to illuminate a sample. The screen is configured to vary a wavelength of the light between a first wavelength and a second wavelength. The first and second wavelengths are different. The system also includes a camera configured to capture a first image of the sample while the sample is illuminated with the light at the first wavelength and to capture a second image of the sample while the sample is illuminated with the light at the second wavelength. The system also includes a computing system configured to combine the first and second images to produce a multispectral image, measure a spectral feature in the multispectral image, and determine that a person from whom the sample was taken is at increased risk for a condition based at least partially upon the spectral feature.

BRIEF DESCRIPTION OF THE FIGURES

FIG. 2A illustrates an image of a sample of stool with hemoglobin therein, and FIG. 2B illustrates an image of a sample of stool alone (i.e., with no hemoglobin), according to an embodiment.

FIG. 3 illustrates a graph showing the sample of stool with hemoglobin versus the sample of stool alone, according to an embodiment.

DETAILED DESCRIPTION OF THE PREFERRED EMBODIMENTS

The presently disclosed subject matter now will be described more fully hereinafter with reference to the accompanying Drawings, in which some, but not all embodiments of the disclosures are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

Camera-Based Hemoglobin Detection

Figure 1:
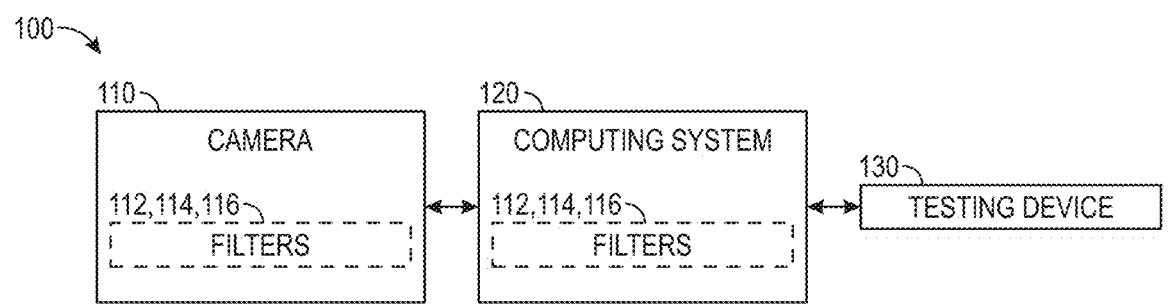
FIG. 1 illustrates a schematic view of a system for identifying a molecule in a sample, according to an embodiment.

FIG. 1 illustrates a schematic view of a system 100 for identifying a molecule in a sample, according to an embodiment. The molecule may be or include hemoglobin, bilirubin, calprotectin, albumin, fatty acid, hydrogen sulfide, and others. The sample may be or include stool, urine, saliva, another biologic specimen, or a combination thereof. FIG. 2A illustrates an image 200A of a sample 210A of stool with hemoglobin therein, and FIG. 2B illustrates an image 200B of a sample 210B of stool alone (i.e., with no hemoglobin), according to an embodiment.

The system 100 may include a camera 110, a computing system 120, and a testing device 130. In one embodiment, the camera 110, the computing system 120, the testing device 130, or a combination thereof may be co-located in a single device. For example, at least a portion of the system 100 may include, be a part of, or connect to a smartphone, a tablet, a laptop, or the like. The camera 110 may be configured to capture one or more images (e.g., images 200A, 200B) of the sample (e.g., sample 210A, 210B), which may or may not have the molecule therein. One or more filters (e.g., three are shown: 112, 114, 116) may be applied as part of the capture of the images 200A, 200B. In one embodiment, the filters 112, 114, 116, may be applied to the lens of the camera 110. For example, the filters 112, 114, 116 may be or include thin film filters that cover the lens of the camera 110. The film filters may be changed manually so that three images may be captured of a single sample—one image with each filter. In another embodiment, the filters 112, 114, 116 may be built (e.g., directly) into the CCD focal plane of the camera 110. In yet another embodiment, a Bayer pattern filter array may be used. In yet another embodiment, the filters 112, 114, 116 may be applied to the images 200A, 200B by the computing system 120.

Figure 4:
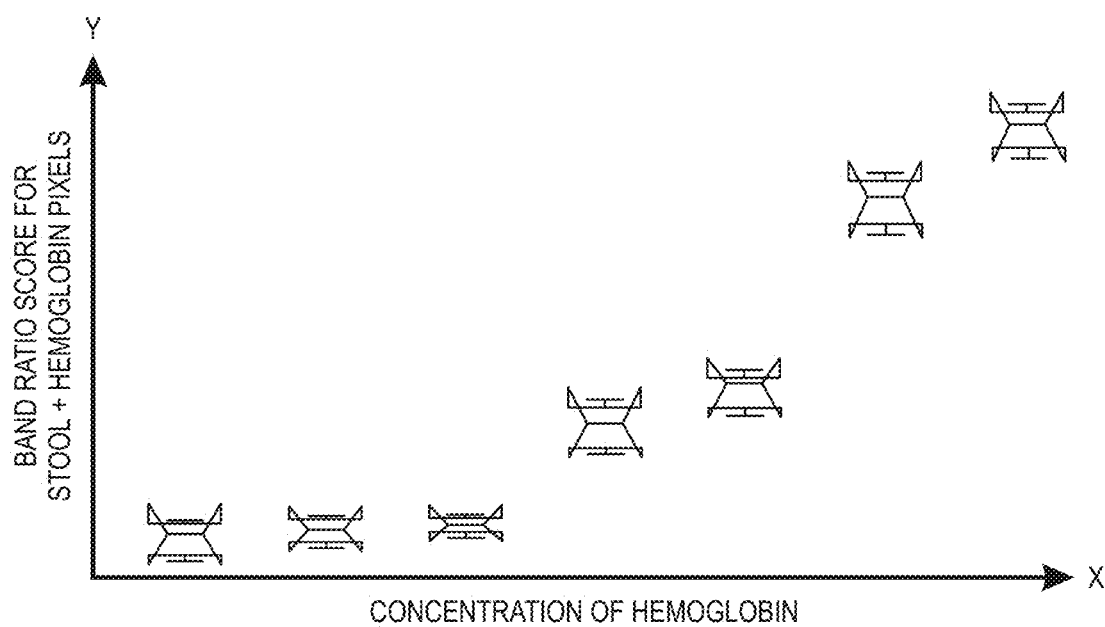
FIG. 4 illustrates a graph showing the dose response in hemoglobin detection as the concentration of the hemoglobin in stool increases, according to an embodiment.

The computing system 120 may be configured to analyze the images 200A, 200B to detect the presence and/or amount of the molecule (e.g., hemoglobin) in the sample (e.g., stool). More particularly, the computing system 120 may be configured to detect a unique spectral signature of the molecule to differentiate between a sample with the molecule versus a sample without the molecule. FIG. 3 illustrates a graph showing the sample 210A of stool with hemoglobin versus the sample 210B of stool alone, according to an embodiment. In one example, as the amount of the molecule in the sample increases, the detectability of the molecule also increases in a dose response manner. This is shown in FIG. 4, which illustrates a graph showing the dose response in hemoglobin detection as the concentration of the hemoglobin in stool increases, according to an embodiment. More particularly, the ratio of specific wavelength features and a quantitative comparison of these resulting values across multiple types of computations may help to distinguish samples with hemoglobin from those without.

The testing device 130 may be or include a fecal immunochemical test (FIT) device or other diagnostic test/information. The testing device 130 may test for the molecule (e.g., hemoglobin) in the sample (e.g., stool) before, simultaneously with, or after the camera 110 and the computing system 120 attempt to detect the presence and/or amount of the molecule in the sample. For example, the testing device 130 may be configured to connect to the computing system 120 and to serve as a secondary testing system for the molecule after the camera 110 and the computing system 120 perform image-based detection.

Figure 5:
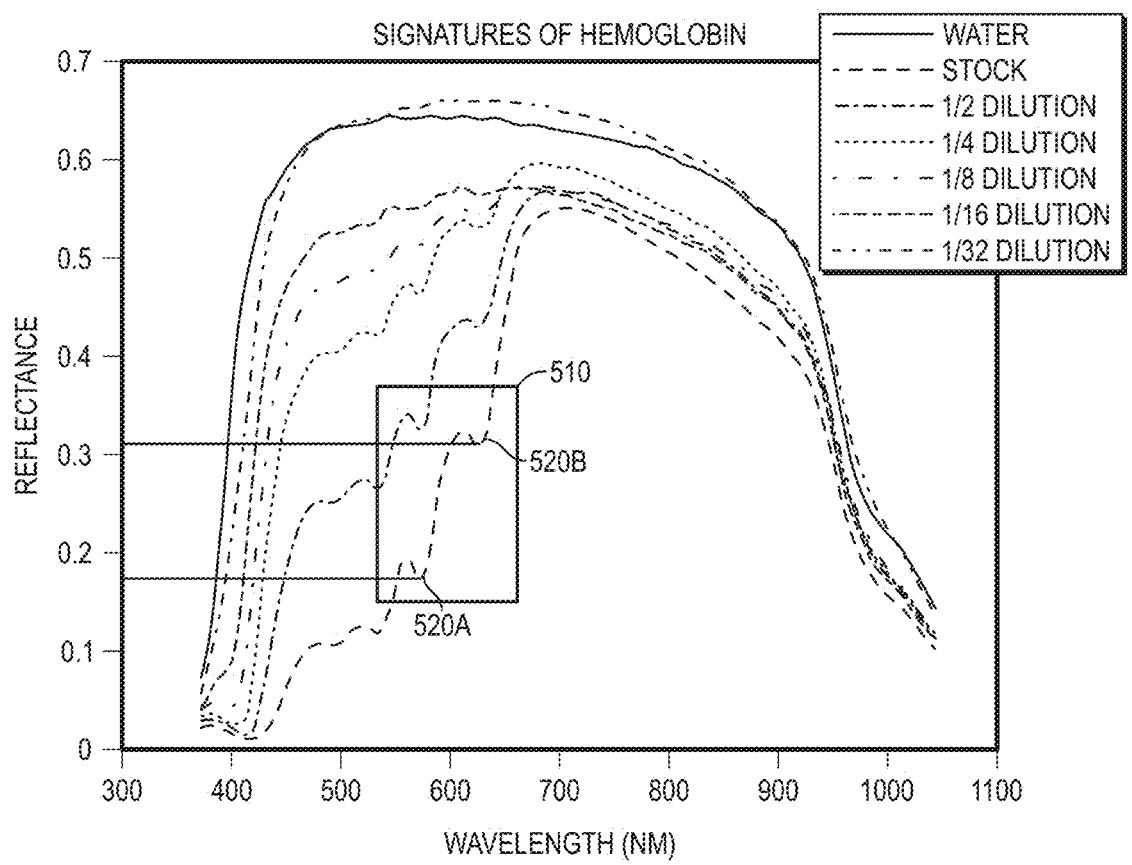
FIG. 5 illustrates a graph showing reflectance versus wavelength of hemoglobin at a plurality of different concentrations, according to an embodiment.

FIG. 5 illustrates a graph showing reflectance versus wavelength of hemoglobin at a plurality of different concentrations, according to an embodiment. Each hemoglobin curve may have one or more spectral signatures (e.g., also referred to as features and/or fingerprints) 510 that may be used to detect its presence in various types of samples. The spectral signature 510 may resemble the letter V (also referred to as a V-feature) and/or the letter W (also referred to as a W-feature). The spectral signature 510 may be present within a predetermined wavelength range. The predetermined wavelength range may be from about 450 nm to about 690 nm, about 575 nm to about 625 nm, or about 600 nm to about 650 nm.

As described in greater detail below, the computing system 120 may implement a spectral processing algorithm on the images 200A, 200B to detect the presence of the spectral signature 510 for the molecule (e.g., hemoglobin). To accomplish this, the algorithm may utilize spectral continuum removal and/or band-ratio analysis. The continuum removal may use linear interpolation to remove the slope of the spectral signature 510 while maintaining one or more spectral absorption features 520A, 520B. As used herein, a spectral absorption feature refers to a change in shape of the spectral curve. The continuum removal may be performed within the predetermined wavelength range.

After the continuum removal is performed, the band ratio may then be determined for one or more of the absorption features 520A, 520B to measure the ratio of the absorption feature 520A, 520B, which indicates the amount of the chemical associated with the absorption feature 520A, 520B that is present in the sample. In one embodiment, the reflectance value for the point 520B may represent the numerator, and the reflectance value for the point 520A may be the denominator. The ratio (e.g., numerator/denominator) may be greater than or equal to 1 to be positive (i.e., hemoglobin present).

Figure 6:
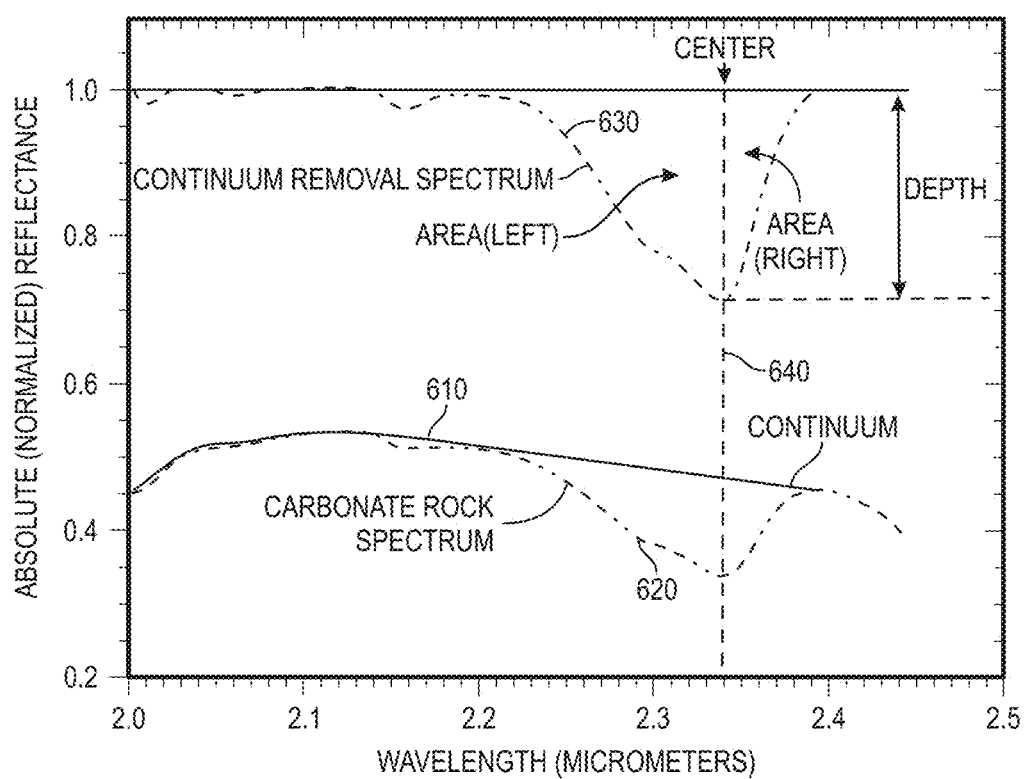
FIG. 6 illustrates a graph showing the detection of a spectral signature in the image, according to an embodiment.

FIG. 6 illustrates a graph showing the detection of a spectral signature in the image, according to an embodiment. The line 610 represents the measured spectrum (e.g., from spectral signature 510). Using interpolation, the spectrum 620 may be determined, which is a measure of the continuum (e.g., the overall shape) of the measured spectrum 610.

The curve 630 may be determined by dividing the spectrum 620 by the spectrum 610. This is referred to as the continuum removal, which effectively removes the overall shape of the measured spectrum 610 and preserves (e.g., enhances) the spectral features (e.g., spectral absorption features 520A, 520B). From the continuum-removed spectrum 630, the spectral depth may be determined using band ratios, as shown along the dashed vertical line 640.

Figure 7:
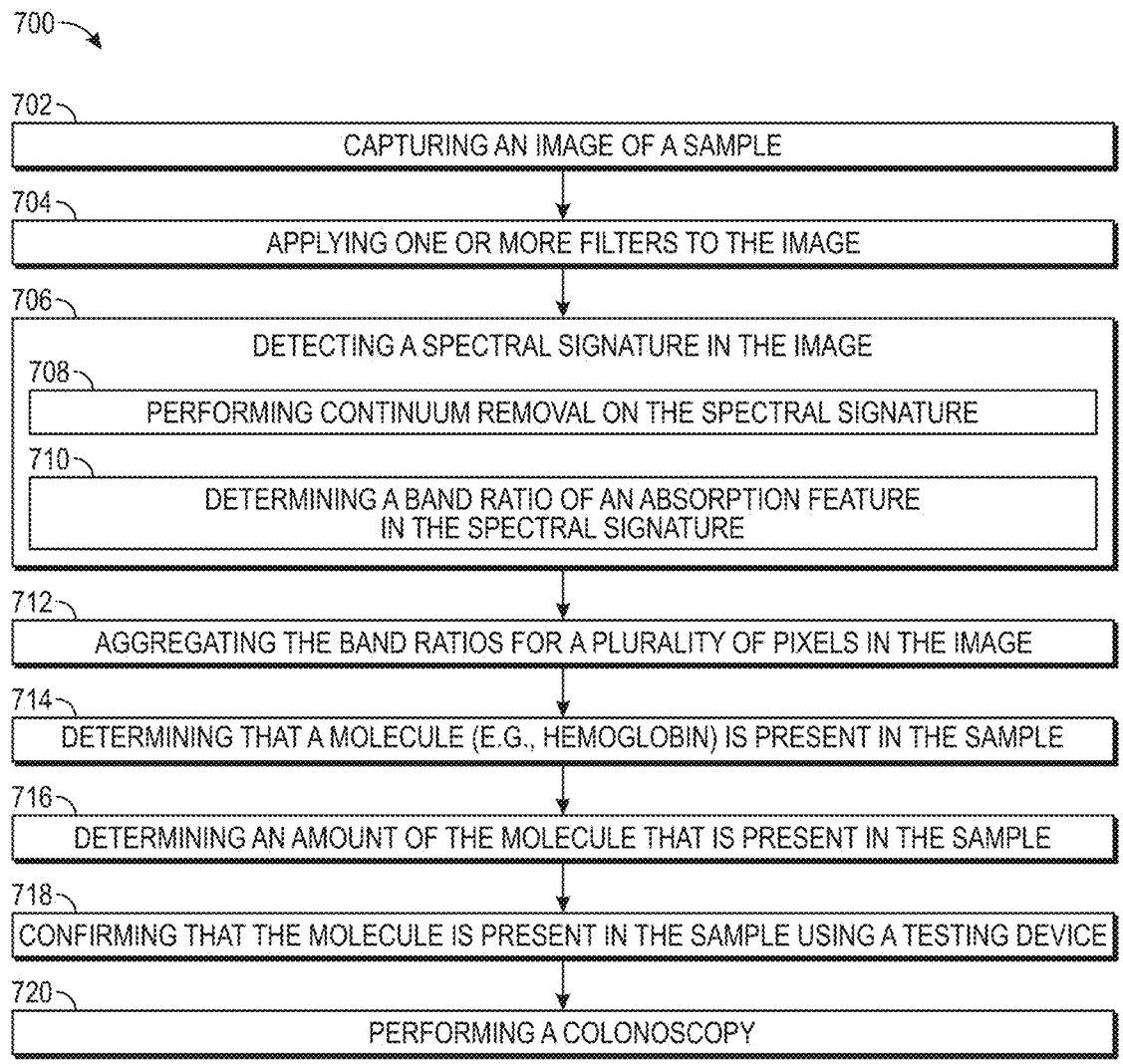
FIG. 7 illustrates a flowchart of a method for detecting a molecule in a sample, according to an embodiment.

FIG. 7 illustrates a flowchart of a method 700 for detecting a molecule in a sample, according to an embodiment. An illustrative order of the method 700 is provided below; however, one or more steps of the method 700 may be performed in a different order, combined, split into substeps, repeated, or omitted. One or more steps of the method 700 may be performed by the system 100.

The method 700 may include capturing one or more images of a sample, as at 702. For example, this may include capturing the image 200A that includes the sample 210A. The image 200A may be captured with the camera 110.

The method 700 may also include applying one or more filters 112, 114, 116 to the image(s) 200A, as at 704. As mentioned above, the filters 112, 114, 116 may be applied to the camera 110 and/or by the computing system 120. The filters 112, 114, 116 may be or include bandpass filters that are configured to pass the predetermined wavelength range. As mentioned above, for hemoglobin, the predetermined wavelength range may be from about 450 nm to about 690 nm, about 575 nm to about 625 nm, or about 600 nm to about 650 nm.

The filters 112, 114, 116 may each be configured to pass different wavelengths. The first filter 112 may be configured to pass a first wavelength, the second filter 114 may be configured to pass a second wavelength, and the third filter 116 may be configured to pass a third wavelength. The third wavelength may be between the first and second wavelengths. In one example, the first wavelength may be from about 639 nm to about 647 nm, the second wavelength may be from about 623 nm to about 631 nm, and the third wavelength may be from about 628 nm to about 636 nm. In another example, the first wavelength may be about 643 nm, the second wavelength may be about 627 nm, and the third wavelength may be about 632 nm.

The method 700 may also include detecting a spectral signature 510 in the image(s) 200A, as at 706. The spectral signature 510 (e.g., V-shape and/or W-shape) may be detected by the computing system 120. The spectral signature 510 may be detected after the filters 112, 114, 116 are applied to the image 200A. The spectral signature 510 may be specific to the molecule (e.g., hemoglobin) that is being detected. As mentioned, the spectral signature 510 may include one or more absorption features 520A, 520B.

In one embodiment, detecting the spectral signature 510 may include performing continuum removal on the spectral signature 510, as at 708. The continuum removal may be performed within the predetermined wavelength range. The continuum removal may be performed using linear interpolation to remove a slope from the spectral signature 510 while maintaining the absorption feature(s) (e.g., absorption feature 520A). In one example, performing the continuum removal may include:

$$w*r(\lambda 1)+(1-w)*r(\lambda 2) \qquad \text{Equation 1}$$

where w represents a weight value, $r(\lambda 1)$ represents the value of the spectrum of the absorption feature 520A at the first wavelength, and $r(\lambda 2)$ represents the value of the spectrum of the absorption feature 520A at the second wavelength. The weight value w may be specific for the particular molecule to be detected. For example, the weight value w may be 0.5156 for hemoglobin.

In other words, performing the continuum removal may include determining a first product of a weight and a value of a spectrum of the absorption feature 520A at the first wavelength, determining a second product of a complement of the weight and a value of the spectrum of the absorption feature 520A at the second wavelength, and determining a sum of the first product and the second product.

Detecting the spectral signature 510 may also or instead include determining a band ratio of an absorption feature 520A in the spectral signature 510, as at 610. The band ratio may be determined after the continuum removal is performed. In one example, the band ratio may include:

$$\text{Band ratio}=(w*r(\lambda 1)+(1-w)*r(\lambda 2))/r(\lambda 3) \qquad \text{Equation 2}$$

where $r(\lambda 3)$ represents the value of the spectrum of the absorption feature 520A at the third wavelength. In other words, the numerator of the band ratio may include the sum (from Equation 1), and the denominator of the band ratio may include the value of the spectrum of the absorption feature 520A at the third wavelength.

In one embodiment, the image 200A may include a plurality of pixels, and the spectral signature 510 may be detected (e.g., the band ratio may be determined) for one or more of the pixels. For example, the spectral signature 510 may be detected (e.g., the band ratio may be determined) for all of the pixels in the image 200A.

The method 700 may also include aggregating the band ratios for the pixels in the image 200A, as at 712. One or more techniques may be used to aggregate the band ratios. For example, one technique includes aggregating or counting the number of values above a specific threshold, and another technique includes aggregating or counting values over a specific spatial area. In one embodiment, one of the techniques may be used when the concentration of the molecule in the sample is below a predetermined concentration threshold, and the other technique may be used when the concentration of the molecule in the sample is above the predetermined concentration threshold. In another embodiment, multiple techniques may be combined to create a composite.

The method 700 may also include determining that the molecule (e.g., hemoglobin) is present in the sample 210A, as at 714. The determination that the molecule is present may be based at least partially upon the detection of the spectral signature 510, the determination of the band ratio, the aggregation of the band ratios, or a combination thereof. The method 700 may be able to detect a predetermined mass of the molecule (e.g., hemoglobin) within one gram of the sample 210A (e.g., stool+hemoglobin). The predetermined mass may be from about 5 micrograms to about 10 micrograms or about 10 micrograms to about 20 micrograms, which is less than or equal to the threshold used by conventional FIT tests in the United States (i.e., 20 micrograms hemoglobin/gram stool).

The method 700 may also include determining an amount of the molecule that is present in the sample 210A, as at 716. The determination of the amount of the molecule that is present may be based at least partially upon the detection of the spectral signature 510, the determination of the band ratio, the aggregation of the band ratios, other mathematical approaches, or a combination thereof. In another embodiment, the determination of the amount of the molecule that is present may be a function of the band ratio scores from the pixels of the sample. The use of "function" can represent any algorithm that takes as input the band ratio scores and generates a number that is assigned to the sample.

The method 700 may also include confirming that the molecule (e.g., hemoglobin) is present in the sample 210A using the testing device 130, as at 718. This may also or instead include determining an amount of the molecule that is present in the sample 210A using the testing device 130. This step may occur before, simultaneously with, or after one or more of the steps 702-716. For example, this step may occur in response to the image-based determination(s) at step 714 and/or step 716.

In another embodiment, instead of or in addition to using the testing device 130 (e.g., a FIT test), additional diagnostic information may be obtained for the patient. For example, the patient history or lab data for the patient may be used to generate a composite score that includes multiple risk variables beyond spectral and FIT alone.

The method 700 may also include performing a colonoscopy, as at 720. The colonoscopy may be performed at least partially in response to the determination that the molecule is present (at 714), the determination of the amount of the molecule that is present (at 716), the determination that the molecule is present (at 718), or a combination thereof.

Capturing Multi-Spectral Images

Conventional digital cameras may be configured to capture broad bands of the wavelength spectrum. For example, the bandwidth of the red, green, and/or blue channels of conventional color digital cameras is over 100 nanometers, while spectral features of interest span tens of nanometers. The resulting image from the conventional camera represents a composite and/or integrated intensity level. For example, the intensity of a pixel for conventional color digital cameras is an average of the intensities over the entire bandwidth of the red, green, and/or blue channels. As a result, the ability to characterize the intensity (e.g., of the pixels in the image) at specific wavelengths has not been conventionally possible.

The system and method described herein may be configured to capture a multi-spectral image using a camera (e.g., the camera 110) without any additional hardware additions or modifications. The system and method may also be configured to characterize the intensity (e.g., of the pixels in the image) at specific wavelengths. Knowing the intensity at specific wavelengths may provide unique characteristics that can be used for detection and/or identification purposes. For example, the system and method may be used to detect hemoglobin in the sample (e.g., sample 210A, 210B). As mentioned above, the sample 210A, 210B may be or include stool, urine, saliva, another biologic specimen, or a combination thereof.

Figure 8:
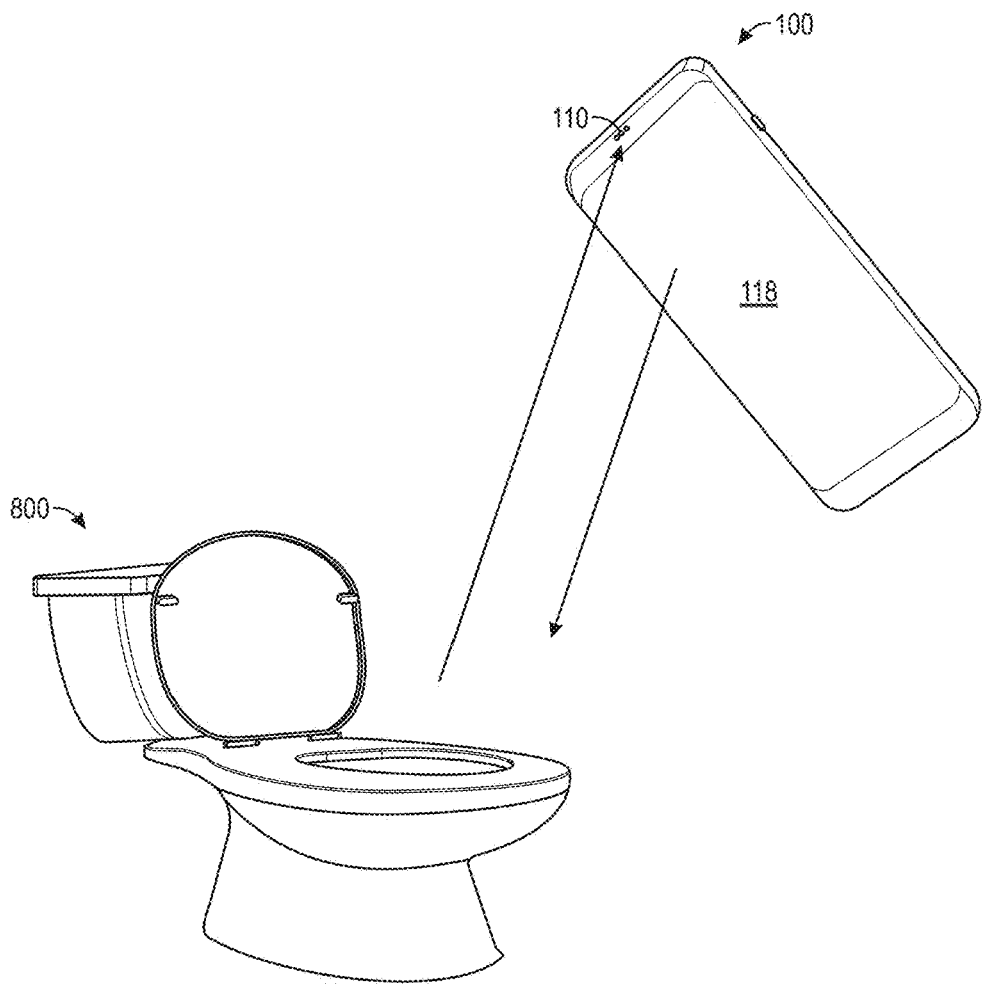
FIG. 8 illustrates a schematic view of the system (e.g., from FIG. 1) capturing an image of the sample in a toilet, according to an embodiment.

FIG. 8 illustrates a schematic view of the system 100 (e.g., the camera 110) capturing an image (e.g., image 200A, 200B) of the sample (e.g., sample 210A, 210B) of stool in a toilet 800, according to an embodiment. As mentioned above, the system 100 (e.g., the camera 110) may include, be a part of, or connect to a smartphone, a tablet, a laptop, or the like. In the embodiment shown in FIG. 8, the system 100 is a smartphone, and the camera 110 is located on a front side of the smartphone (e.g., the same side as the screen 118). For example, the camera 110 may be located above the screen 118. Although not shown, the system 100 may also or instead use the flashlight and/or a second camera, which may both be located on a back side of the smartphone.

As shown in FIG. 8, the camera 110 and the screen 118 may face the sample (e.g., in the toilet 800). The screen 118 may be used as a light source. The wavelengths of the light may be adjusted using software in the system 100 to emit light in a narrow-band of frequencies. The light may then reflect off the sample, the toilet 800, the water in the toilet 800, or a combination thereof in the camera's field of view, and then be captured by the camera 110. This may be referred to as active imaging. The image(s) captured by the camera 110 may be or include one or more, two or more, or three or more narrowband (tens of nanometers) image(s) whose intensity at specific wavelengths can be used for many diagnostic or detection purposes. For example, the bandwidth in each image and/or each pixel may be 100 nanometers or less, 50 nanometers or less, 20 nanometers or less, or 10 nanometers or less. Applying this approach clinically may permit the non-invasive detection of biomarkers (e.g., hemoglobin) with known spectral fingerprints and/or wavelength patterns in a variety of human samples such as stool, saliva, sweat, blood, urine, and skin among others.

Figure 9:
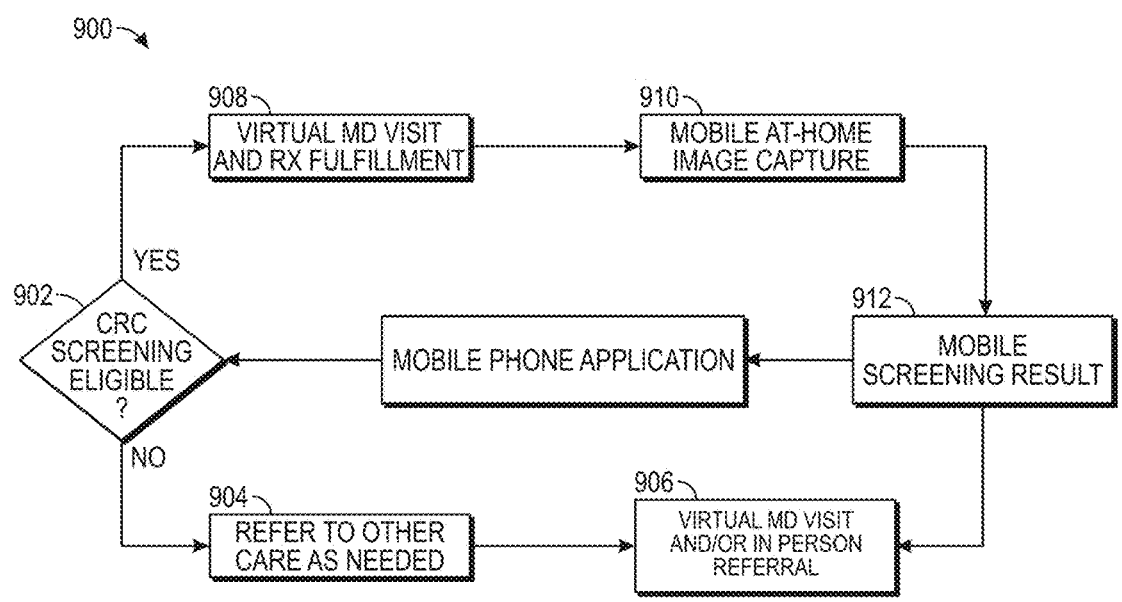
FIG. 9 illustrates a flowchart of a method for performing a colorectal cancer (CRC) screening, according to an embodiment.

FIG. 9 illustrates a flowchart of a method 900 for performing a colorectal cancer (CRC) screening, according to an embodiment. An illustrative order of the method 900 is provided below; however, one or more steps of the method 900 may be performed in a different order, combined, split into sub-steps, repeated, or omitted. One or more steps of the method 900 may be performed by the system 100.

The method 900 may include determining whether the patient is eligible for a CRC screening, as at 902. The patient may be determined to be eligible in response to the patient being greater than a predetermined age. The patient may also or instead be eligible in response to noticing irregularities (e.g., blood) in the patient's stool or urine.

If the patient is not eligible, then the patient may be referred to other care, as at 904. The patient may also or instead visit a doctor in person or virtually, as at 906.

If the patient is eligible, the method 900 may proceed to visiting a doctor in person or virtually, as at 908. This may also or instead include fulfilling a prescription related to colorectal cancer screening.

The method 900 may also include capturing one or more images (e.g., images 200A, 200B) of a sample (e.g., sample 210A, 210B) of stool using the system 100, as at 910. This may be done at home. The sample may be processed by the system 100 to produce a result, as at 912. The patient may be directed to visit a doctor in person or virtually in response to the result, as at 906.

Figure 10:
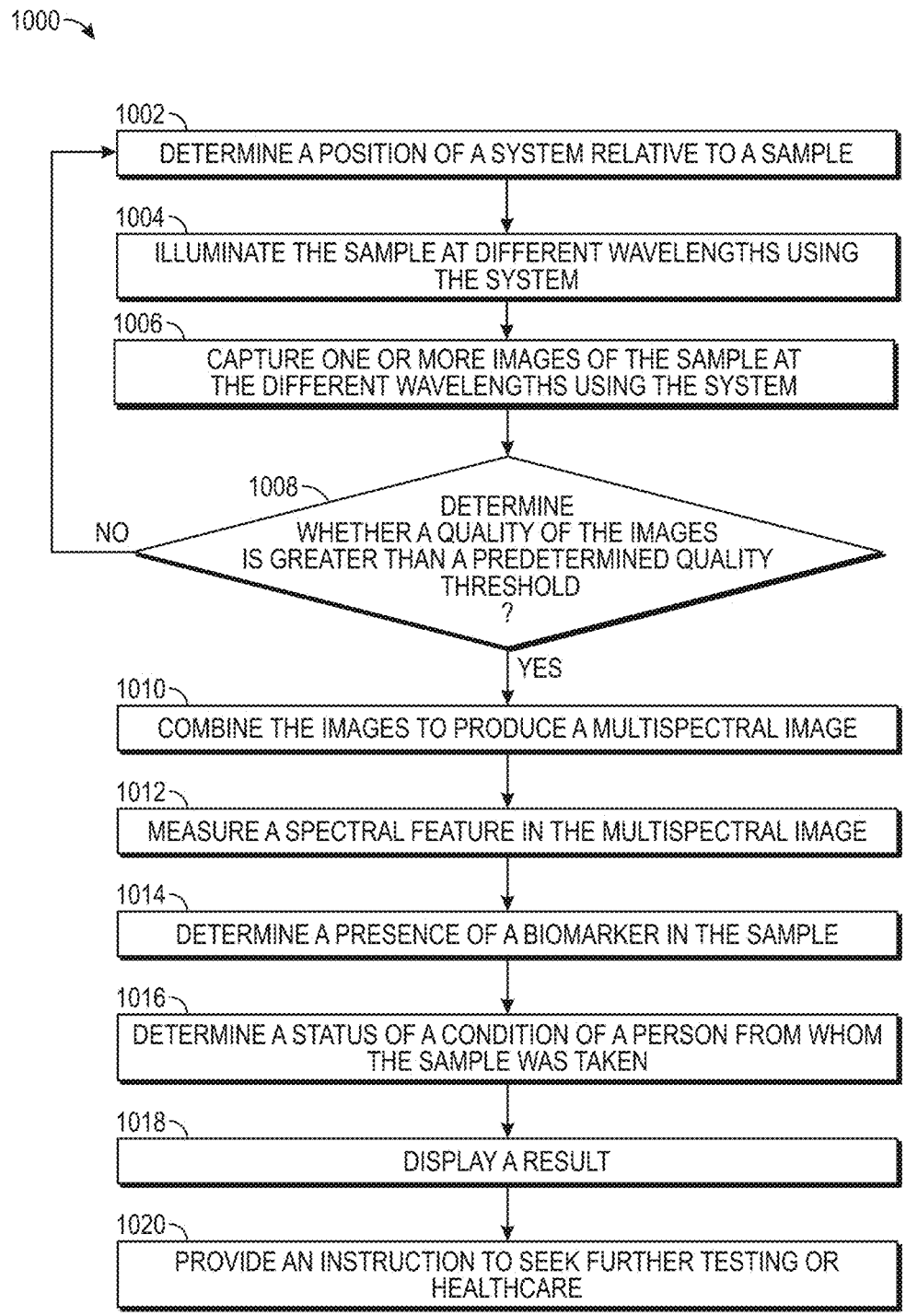
FIG. 10 illustrates a flowchart of another method for performing a colorectal cancer (CRC) screening, according to an embodiment.

FIG. 10 illustrates a flowchart of a method 1000 for performing a colorectal cancer (CRC) screening, according to an embodiment. An illustrative order of the method 1000 is provided below; however, one or more steps of the method 1000 may be performed in a different order, combined, split into sub-steps, repeated, or omitted. One or more steps of the method 1000 may be performed by the system 100.

The method 1000 may include determining a position of the system 100 relative to the sample (e.g., sample 210A, 210B), as at 1002. More particularly, user/patient may point the front of the system (e.g., smartphone) 100 toward the sample in the toilet 800 so that the camera 110 and the screen 118 face the sample in the toilet 800. The system 100 may be configured to determine a distance between the system 100 (e.g., the camera 110 and/or screen 118) and the sample and/or toilet 800. The system 100 may also or instead be configured to determine an angle between the system 100 (e.g., the camera 110 and/or screen 118) and the sample and/or toilet 800. The system 100 may compare the measured distance and/or angle to a predetermined (e.g., optimal) distance and/or angle and then instruct the user/patient to move the system 100 to optimize the distance and/or angle.

The method 1000 may also include illuminating the sample with the system 100, as at 1004. More particularly, this may include illuminating the sample in the toilet 800 using the light from the screen 118. The sample may be illuminated at a plurality of different wavelengths, either one wavelength at a time or multiple different wavelengths simultaneously. For example, the sample may first be illuminated by a first wavelength, and then the sample may subsequently (or simultaneously) be illuminated by a second wavelength. In at least one embodiment, the sample may also subsequently (or simultaneously) be illuminated by a third wavelength. One of the wavelengths may be in the red spectrum from about 575 nm to about 675 nm (e.g., about 625 nm). Another of the wavelengths may be in the green spectrum from about 475 nm to about 575 nm (e.g., about 525 nm). Optionally, another of the wavelengths may be in the blue spectrum from about 420 nm to about 500 nm (e.g., about 460 nm).

The method 1000 may also include capturing one or more images (e.g., images 200A, 200B) of the sample(s) using the system 100, as at 1006. More particularly, this may include capturing a plurality of images at a plurality of different wavelengths, frequencies, and/or intensities using the camera 110. For example, the camera 110 may capture one or more first images of the sample while the light from screen 118 that illuminates and/or reflects off of the sample is at the first wavelength. The camera 110 may also subsequently (or simultaneously) capture one or more second images of the sample while the light from screen 118 that illuminates and/or reflects off of the sample is at the second wavelength. The camera 110 may also subsequently (or simultaneously) capture one or more third images of the sample while the light from screen 118 that illuminates and/or reflects off of the sample is at the third wavelength. Furthermore, the effective wavelength of the illumination from the screen 118 can be adjusted by adding and/or subtracting images that are illuminated by the flash and/or illuminated by the red, green, and/or blue LEDs in the screen 118. As described in greater detail below, these images may form a multi-spectral image that may be analyzed using spectral processing algorithms to detect materials (e.g., biomarkers) of interest.

The method 1000 may also include determining whether a quality of the images is greater than a predetermined quality threshold, as at 1008. The system 100 (e.g., the computing system 120) may determine whether the quality is greater than the predetermined quality threshold. The quality may include a spectral quality and/or a spatial quality. If the quality is less than the predetermined quality threshold, the method 1000 may loop back around to step 1002, 1004, or 1006.

If the quality is greater than the predetermined quality threshold, the method 1000 may proceed to combining the images to produce a multispectral image, as at 1010. More particularly, the system 100 (e.g., the computing system 120) may combine two or more images (or three or more images) that are captured at different wavelengths, frequencies, and/or intensities. The images may be combined via addition, subtraction, division, or a combination thereof.

The method 1000 may also include measuring a spectral feature in the multispectral image, as at 1012. Examples of the spectral features(s) are described above with respect to FIGS. 5-7. The spectral feature(s) may be measured using a spectral processing algorithm running on the system 100 (e.g., the computing system 120). In one embodiment, the spectral feature(s) may be detected and/or measured at every pixel in the multispectral image. In another embodiment, the spectral feature(s) may be measured or detected in the aggregate across a plurality of pixels in the multispectral image. As described below, the spectral feature(s) may be (or be used to detect) biomarkers (e.g., hemoglobin) in the sample.

The method 1000 may also include determining a presence of a biomarker in the sample, as at 1014. More particularly, this may include determining or estimating the presence and/or concentration of one or more biomarkers (e.g., hemoglobin) in the sample 210A, 210B using the spectral processing algorithm running on the system 100 (e.g., the computing system 120). The presence and/or concentration of the biomarker(s) may be based at least partially upon the images, the multispectral image, the spectral feature(s), or a combination thereof. The presence or concentration of the biomarker(s) may convey a possible status of a condition. Illustrative conditions may include increased risk for CRC, absence of blood, presence of inflammation, positive for infection, or the like.

The method 1000 may also include determining a status of a condition of a person whom the sample was taken, as at 1016. The determination may be based at least partially upon the captured images, the multispectral image, the spectral feature(s), the presence and/or concentration of biomarker(s), or a combination thereof. In one embodiment, determining the status may include determining and/or assigning a score (e.g., 70%) to the multispectral image and/or the spectral feature(s) that indicates the presence of one or more biomarkers in the sample. In another embodiment, determining the status may include determining a likelihood that the person has (or is at increased risk for) CRC.

The method 1000 may also include displaying a result, as at 1018. For example, the result may be displayed on the screen 118 of the system 100. The result may be or include the captured images, the multispectral image, the spectral feature(s), the biomarker(s) the likelihood of CRC, a qualitative result (e.g., positive or negative), or a combination thereof. Used in the screening context, the result may indicate a need for further action and/or increased risk for CRC. The result may be shared with a physician.

The method 1000 may also include providing an instruction to seek further testing or healthcare (e.g., to visit a physician), as at 1020. The instruction may be provided by the system 100 in response to the identification of a known biomarker above a predetermined threshold (e.g., 20 micrograms of hemoglobin/gram of stool) used for the purposes of CRC screening.

Although the present disclosure has been described in connection with preferred embodiments thereof, it will be appreciated by those skilled in the art that additions, deletions, modifications, and substitutions not specifically described may be made without departing from the spirit and scope of the disclosure as defined in the appended claims.

The invention claimed is:

1. A method for performing a screening, the method comprising:
   illuminating a sample with light from a screen of a system at a first wavelength while the system is at a predetermined position with respect to the sample;
   capturing a first image of the sample using a camera of the system while the system is at the predetermined position and the sample is illuminated with the light at the first wavelength;
   illuminating the sample with the light from the screen at a second wavelength while the system is at the predetermined position;
   capturing a second image of the sample using the camera while the system is at the predetermined position and the sample is illuminated with the light at the second wavelength;
   combining the first and second images to produce a multispectral image; and
   measuring a spectral feature in the multispectral image.

2. The method of claim 1, further comprising determining a position of the system relative to the sample, wherein the system comprises a phone or a tablet with a front side having the screen and the camera located above the screen, and wherein the sample comprises stool, saliva, sweat, blood, urine, skin, or a combination thereof.

3. The method of claim 2, further comprising instructing a user holding the phone or tablet to move the phone or tablet into the predetermined position in response to the determined position, wherein moving the phone varies a distance between the front side and the sample, varies an angle between the front side and the sample, or both.

4. The method of claim 1, wherein the sample is illuminated with the light at the second wavelength after the first image has been captured.

5. The method of claim 1, wherein the first and second wavelengths are different.

6. The method of claim 1, wherein the first wavelength is from about 575 nm to about 675 nm, and wherein the second wavelength is from about 475 nm to about 575 nm.

7. The method of claim 6, further comprising:
   illuminating the sample with the light from the screen at a third wavelength while the system is at the predetermined position, wherein the first, second, and third wavelengths are different, and wherein the third wavelength is from about 420 nm to about 500 nm;
   capturing a third image of the sample using the camera while the system is at the predetermined position and the sample is illuminated with the light at the third wavelength; and
   combining the first, second, and third images to produce the multispectral image.

8. The method of claim 1, further comprising determining that a person from whom the sample was taken is at increased risk for a condition based at least partially upon the spectral feature.

9. The method of claim 1, further comprising determining a concentration of a biomarker in the sample based at least partially upon the spectral feature, wherein the biomarker comprises hemoglobin, bilirubin, calprotectin, albumin, fatty acid, hydrogen sulfide, or a combination thereof.

10. The method of claim 9, further comprising determining that a person from whom the sample was taken is at increased risk for a condition based at least partially upon the biomarker, wherein the sample comprises stool that is under water in a toilet, wherein the biomarker in the sample comprises hemoglobin, and wherein the condition comprises colorectal cancer (CRC).

11. A method for performing a colorectal cancer (CRC) screening, the method comprising:
   determining a position of a system relative to a sample, wherein the system comprises a phone or a tablet with a front side having a screen and a camera located above the screen, and wherein the sample comprises stool, saliva, sweat, blood, urine, skin, or a combination thereof;
   instructing a user holding the phone or tablet to move the phone or tablet into a predetermined position in response to the determined position, wherein moving the phone or tablet varies a distance between the front side and the sample, varies an angle between the front side and the sample, or both;
   illuminating the sample with the light from the screen at a first wavelength while the phone or tablet is at the predetermined position;
   capturing a first image of the sample using the camera while the phone or tablet is at the predetermined position and the sample is illuminated with the light at the first wavelength;
   illuminating the sample with the light from the screen at a second wavelength while the phone or tablet is at the predetermined position, wherein the sample is illuminated with the light at the second wavelength after the first image has been captured, and wherein the first and second wavelengths are different;
   capturing a second image of the sample using the camera while the phone or tablet is at the predetermined position and the sample is illuminated with the light at the second wavelength;
   combining the first and second images to produce a multispectral image;
   measuring a spectral feature at each pixel in the multispectral image using a spectral processing algorithm running on the system;
   determining a concentration of a biomarker in the sample based at least partially upon the spectral feature, wherein the biomarker comprises hemoglobin, bilirubin, calprotectin, albumin, fatty acid, hydrogen sulfide, or a combination thereof, and
   determining that a person from whom the sample was taken is at increased risk for a condition based at least partially upon the concentration of the biomarker.

12. The method of claim 11, wherein the sample comprises stool, wherein the biomarker in the sample comprises hemoglobin, and wherein the condition comprises colorectal cancer (CRC).

13. The method of claim 11, wherein the sample is located under water in a toilet.

14. The method of claim 11, further comprising displaying the first image, the second image, the multispectral image, the spectral feature, the biomarker, the concentration of the biomarker, or a combination thereof on the screen.

15. The method of claim 11, further comprising providing an instruction to seek further testing or healthcare in response to the concentration of the biomarker being above a predetermined threshold.

16. A system for performing a screening, the system comprising:
   a screen configured to emit light to illuminate a sample, wherein the screen is configured to vary a wavelength of the light between a first wavelength and a second wavelength, wherein the first and second wavelengths are different;

a camera configured to capture a first image of the sample while the sample is illuminated with the light at the first wavelength and to capture a second image of the sample while the sample is illuminated with the light at the second wavelength; and a computing system configured to:
  combine the first and second images to produce a multispectral image;
  measure a spectral feature in the multispectral image; and
  determine that a person from whom the sample was taken is at increased risk for a condition based at least partially upon the spectral feature.

17. The system of claim 16, wherein the system comprises a phone or a tablet with a front side having the screen and the camera located above the screen.

18. The system of claim 17, wherein the computing system is also configured to determine a concentration of a biomarker in the sample based at least partially upon the spectral feature, wherein the determination that the person from whom the sample was taken is at increased risk for the condition is based at least partially upon the concentration of the biomarker.

19. The system of claim 18, wherein the sample comprises stool that is under water in a toilet, wherein the biomarker in the sample comprises hemoglobin, and wherein the condition comprises colorectal cancer (CRC).

20. The system of claim 19, wherein the screen is further configured to display the first image, the second image, the multispectral image, the spectral feature, the biomarker, the concentration of the biomarker, or a combination thereof after the sample has been illuminated and the first and second images have been captured.

* * * * *